United States Patent
Meridew

(10) Patent No.: US 9,220,599 B2
(45) Date of Patent: Dec. 29, 2015

(54) ACETABULAR CUP HAVING DEFORMATION RESISTANT FEATURES

(75) Inventor: Jason D. Meridew, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 675 days.

(21) Appl. No.: 12/862,369

(22) Filed: Aug. 24, 2010

(65) Prior Publication Data

US 2012/0053699 A1 Mar. 1, 2012

(51) Int. Cl.
*A61F 2/34* (2006.01)
*A61F 2/30* (2006.01)
*A61F 2/32* (2006.01)

(52) U.S. Cl.
CPC ......... *A61F 2/34* (2013.01); *A61F 2002/30013* (2013.01); *A61F 2002/30014* (2013.01); *A61F 2002/30029* (2013.01); *A61F 2002/30077* (2013.01); *A61F 2002/30321* (2013.01); *A61F 2002/30332* (2013.01); *A61F 2002/30354* (2013.01); *A61F 2002/30367* (2013.01); *A61F 2002/30383* (2013.01); *A61F 2002/30448* (2013.01); *A61F 2002/30451* (2013.01); *A61F 2002/30495* (2013.01); *A61F 2002/30654* (2013.01); *A61F 2002/3291* (2013.01); *A61F 2002/3403* (2013.01); *A61F 2002/3404* (2013.01); *A61F 2002/3422* (2013.01); *A61F 2002/3445* (2013.01); *A61F 2002/3448* (2013.01); *A61F 2310/00023* (2013.01); *A61F 2310/00029* (2013.01)

(58) Field of Classification Search
CPC .............................................. A61F 2002/3448
See application file for complete search history.

(56) References Cited

U.S. PATENT DOCUMENTS

| 3,698,017 A | 10/1972 | Scales et al. |
| 3,903,549 A | 9/1975 | Deyerle |
| 3,918,102 A | 11/1975 | Eichler |
| 4,623,352 A * | 11/1986 | Oh .............................. 623/22.28 |

(Continued)

FOREIGN PATENT DOCUMENTS

FR 2705883 A1 * 12/1994 ................ A61F 2/30

OTHER PUBLICATIONS

Machine translation of FR2705883A1, accessed Aug. 5, 2014, 16 pages.*

(Continued)

*Primary Examiner* — Yashita Sharma
*Assistant Examiner* — Rebecca Preston
(74) *Attorney, Agent, or Firm* — Schwegman Lundberg & Woessner, P.A.

(57) ABSTRACT

An acetabular cup component can include a hemispherical first shell, an annular ring, and a second shell. The annular ring can laterally extend from and circumscribe an outer surface of the first shell and can include a first portion for engaging an anatomy. The second shell can include a second portion for engaging the anatomy adjoining the first portion. Another acetabular cup component can include a first shell, a second shell, and a support ring. The support ring can be coupled to an end portion of the first shell and can include a portion for engaging an anatomy and a rim for engaging a bearing. Another acetabular cup component can include a hemispherical inner shell composed of Cobalt, a hemispherical intermediate shell coupled to an outer surface of the inner shell by a diffusion bond, and a hemispherical outer shell coupled to an outer surface of the intermediate shell.

13 Claims, 6 Drawing Sheets

(56) References Cited

U.S. PATENT DOCUMENTS

| | | | |
|---|---|---|---|
| 4,666,449 A | 5/1987 | Frey et al. | |
| 4,784,663 A * | 11/1988 | Kenna | 623/22.29 |
| 5,263,988 A * | 11/1993 | Huebner | 623/22.29 |
| 5,376,120 A | 12/1994 | Sarver et al. | |
| 6,093,208 A * | 7/2000 | Tian | 623/22.2 |
| 6,136,033 A | 10/2000 | Suemer | |
| 6,248,132 B1 * | 6/2001 | Harris | 623/22.15 |
| 6,352,559 B1 | 3/2002 | Church | |
| 6,610,097 B2 | 8/2003 | Serbousek et al. | |
| 6,827,742 B2 | 12/2004 | Hayes, Jr. et al. | |
| 7,192,449 B1 * | 3/2007 | McQueen et al. | 623/22.25 |
| 7,766,971 B2 * | 8/2010 | Gladdish et al. | 623/22.29 |
| 2002/0068980 A1 * | 6/2002 | Serbousek et al. | 623/22.29 |
| 2005/0102034 A1 | 5/2005 | Hayes et al. | |
| 2005/0171614 A1 * | 8/2005 | Bacon | 623/22.19 |
| 2006/0241781 A1 * | 10/2006 | Brown et al. | 623/23.43 |
| 2007/0135927 A1 * | 6/2007 | Harris et al. | 623/22.15 |
| 2007/0173948 A1 | 7/2007 | Meridew et al. | |
| 2007/0203583 A1 | 8/2007 | Slone | |
| 2007/0239283 A1 * | 10/2007 | Berger et al. | 623/22.29 |
| 2009/0005879 A1 | 1/2009 | Tuke et al. | |
| 2009/0018659 A1 * | 1/2009 | Malinin | 623/17.16 |

OTHER PUBLICATIONS

Diffusion Welding, en. Wikipedia.org/wiki/Diffusion-Welding; pg. last modified Jan. 18, 2010.

Regenerex™ Ringloc®+ Modular Acetabular System; Biomet Orthopedics Brochure, pp. 1-10; Aug. 31, 2007.

* cited by examiner

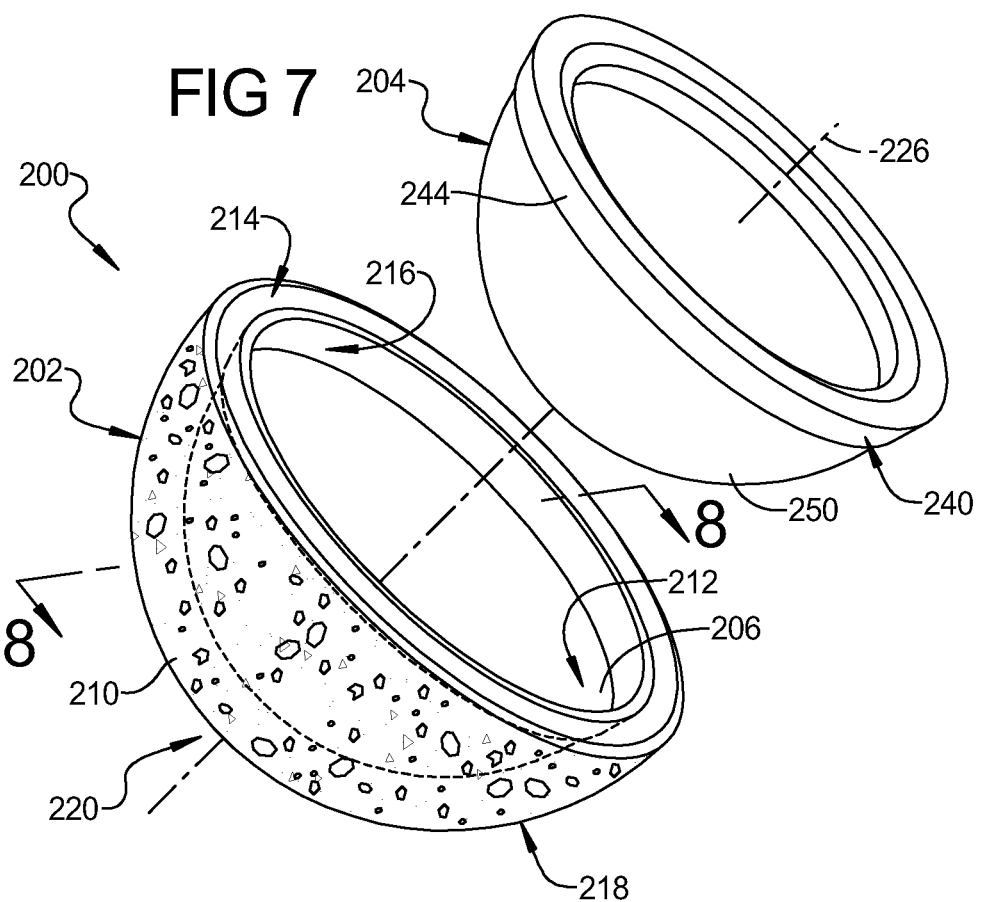
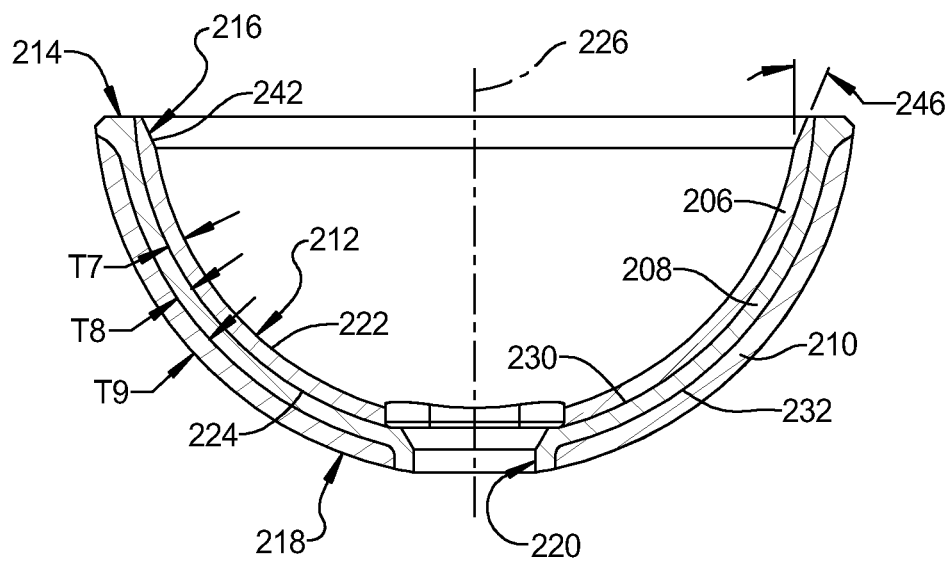

ND RESISTANT FEATURES

ACETABULAR CUP HAVING DEFORMATION RESISTANT FEATURES

FIELD

The present disclosure relates to hip joint prostheses and, more particularly, to acetabular cup prostheses having deformation resistant features.

BACKGROUND

The statements in this section merely provide background information related to the present disclosure and may not constitute prior art.

Articulating regions of the anatomy can include areas where two bone sections move relative to one another. As one example, an acetabulum formed by a hip bone can provide a region for articulating with a head of a femur, or thigh bone. Over time, the articulating region can become injured or worn. Prostheses have been developed to replace the acetabulum and/or the femoral head. When both the acetabulum and the femoral head are replaced, the replacement is generally referred to as a total joint replacement.

The total joint replacement can require an acetabular cup component providing a bearing or articulating surface for the acetabulum and a femoral component providing an articulating surface for the femoral head. The acetabular cup and femoral components can generally be positioned relative to various portions of the associated anatomy in a substantially fixed manner. Portions of the anatomy can be resected or removed in preparation for receiving the associated prosthetic component. The removal of bone material can weaken the anatomy. It is desirable to design prosthetic components capable of handling the loads transmitted through the joint while minimizing the amount of anatomy removed in preparation for receiving the prosthetic component.

SUMMARY

This section provides a general summary of the disclosure and is not a comprehensive disclosure of its full scope or all of its features.

An acetabular cup component for replacing an articulating portion of an anatomy according to the present disclosure can include a hemispherical first shell, an annular ring, and a second shell. The hemispherical first shell can form an interior surface and an outer surface opposite the interior surface. The interior surface can be configured to receive a bearing along a longitudinal axis of the hemispherical first shell. The annular ring can laterally extend from the outer surface of the hemispherical first shell and circumscribe the hemispherical first shell. The annular ring can include a first portion of an exterior surface for engaging the anatomy. The second shell can be coupled to the outer surface of the hemispherical first shell and circumscribe the hemispherical first shell. The second shell can include a second portion of the exterior surface adjoining the first portion.

Another acetabular cup component for replacing an articulating portion of an anatomy according to the present disclosure can include a first shell, a second shell, and a support ring. The first shell can include a hemispherical cup portion and an end portion. The hemispherical cup portion can form an interior surface and an outer surface opposite the interior surface. The interior surface can be configured to receive a bearing along a longitudinal axis of the hemispherical cup portion extending through an apex of the hemispherical cup portion. The end portion can longitudinally extend from an end of the hemispherical cup portion opposite the apex. The end portion can include an engagement surface disposed on an outer circumference of the end portion. The second shell can be coupled to the outer surface of the hemispherical cup portion and circumscribe the hemispherical cup portion. The second shell can include a first portion of an exterior surface for engaging the anatomy. The support ring can be coupled to the end portion via the engagement surface. The support ring can include a second portion of the exterior surface and a rim for engaging the bearing.

Another acetabular cup component for replacing an articulating portion of an anatomy according to the present disclosure can include a hemispherical inner shell, a hemispherical intermediate shell, and a hemispherical outer shell. The hemispherical inner shell can be composed of Cobalt and can have an interior surface and a first outer surface opposite the interior surface. The interior surface can be configured to receive a bearing along a longitudinal axis of the hemispherical inner shell. The hemispherical intermediate shell can have an inner surface coupled to the first outer surface of the hemispherical inner shell and a second outer surface opposite the inner surface. The inner surface can be coupled to the first outer surface by a diffusion bond. The hemispherical intermediate shell can circumscribe the hemispherical inner shell. The hemispherical outer shell can be coupled to the second outer surface of the hemispherical intermediate shell and circumscribe the hemispherical intermediate shell. The hemispherical outer shell can define an exterior surface for engaging the anatomy.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustration purposes only of selected examples and not all possible implementations, and are not intended to limit the scope of the present disclosure in any way.

FIG. 7 is an exploded perspective view of another hip joint prosthesis including an acetabular cup component according to the present disclosure;

FIG. 8 is a cross-sectional view of the acetabular cup component of FIG. 7 taken along line 8-8.

Corresponding reference numerals indicate corresponding parts throughout the several views of the drawings.

DETAILED DESCRIPTION

Figure 1:
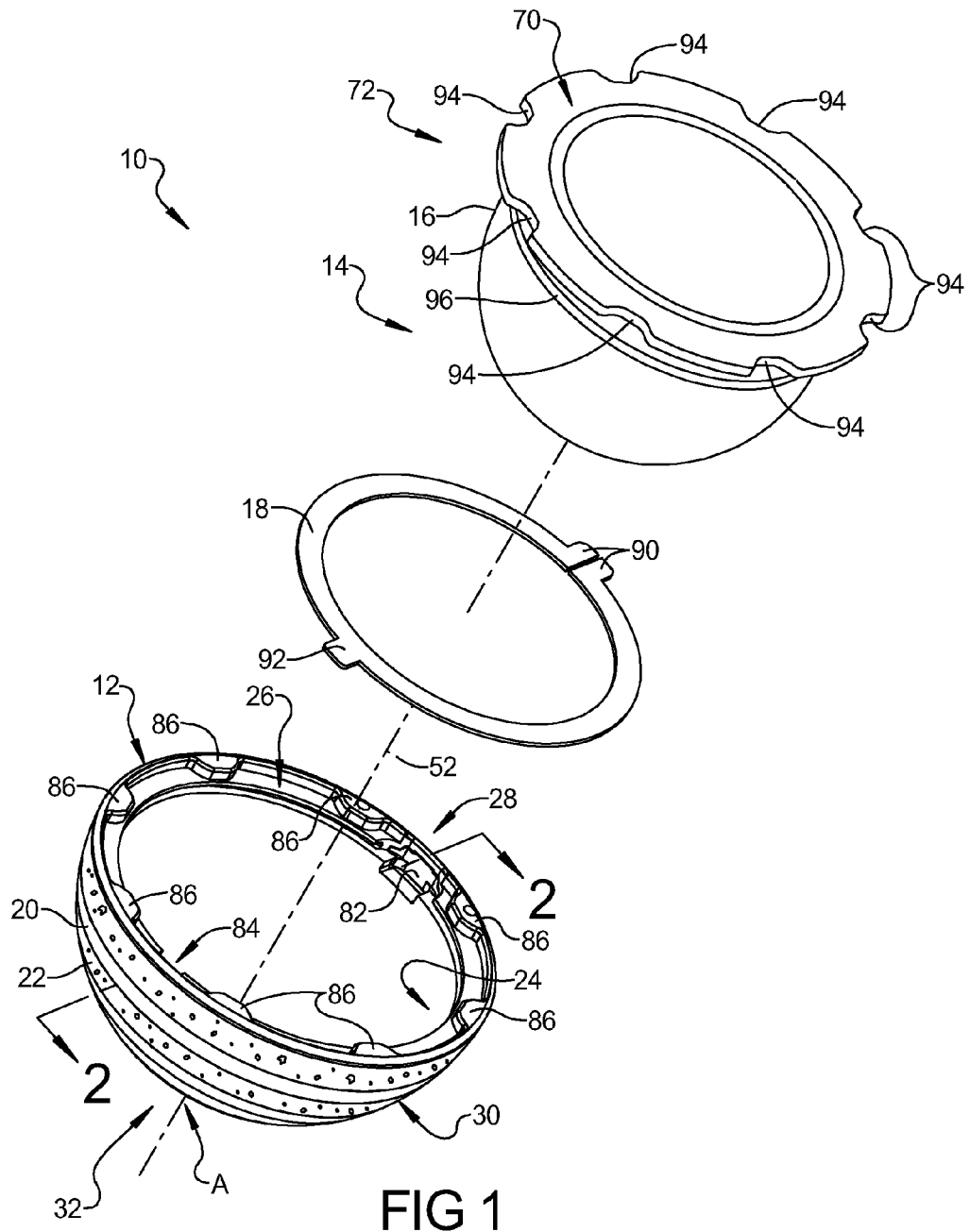
FIG. 1 is an exploded perspective view of a hip joint prosthesis including an acetabular cup component according to the present disclosure.

The following description is merely exemplary in nature and is not intended to limit the present disclosure, its application, or uses. The following description includes a discussion of exemplary acetabular cup components according to the teachings of the present disclosure, however, it should be understood that the discussions are not intended to limit the scope of the appended claims.

For purposes of clarity, corresponding reference numerals will be used throughout the drawings to indicate like or corresponding parts and features.

Prosthetic components can deform when subject to loads transmitted through the joint. The present disclosure provides exemplary acetabular cup components for replacing a portion of the acetabulum that provide improved resistance to deformation over other conventional designs. The acetabular cup components of the present disclosure are thinner in construction than other conventional designs and therefore can be fit into smaller sockets prepared in the hip bone. The acetabular cups can also allow larger femoral head components to be used with the smaller sockets.

Figure 2:
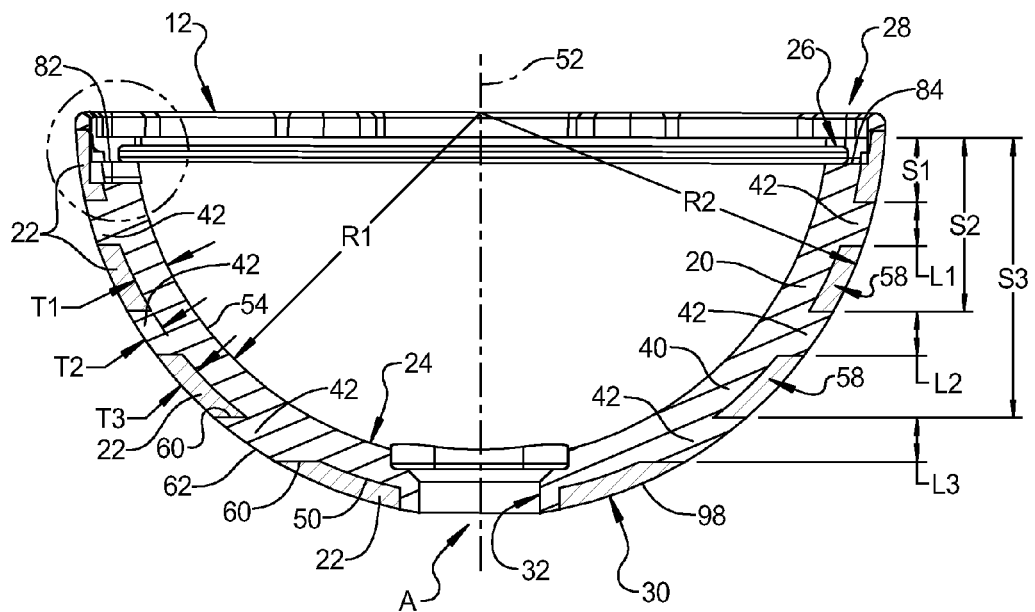
FIG. 2 is a cross-sectional view of the acetabular cup component of FIG. 1 taken along line 2-2.
Figure 3:
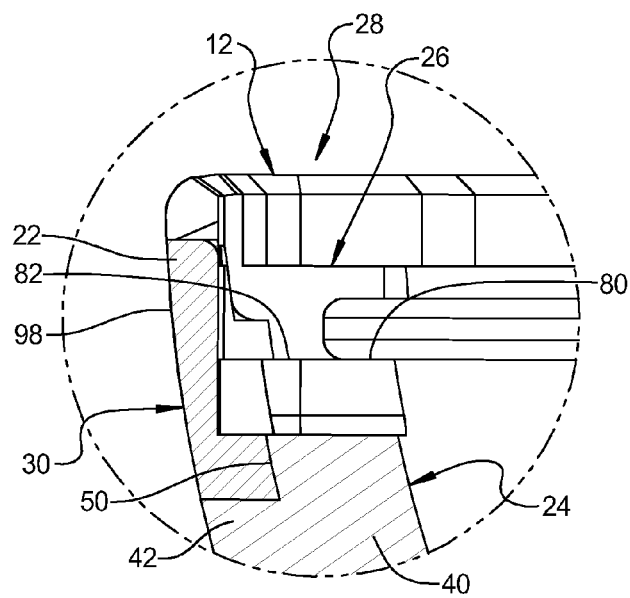
FIG. 3 is an enlarged cross-sectional view of a portion of the acetabular cup component of FIG. 1.

With reference to FIGS. 1-3, an exemplary hip joint prosthesis 10 including an acetabular cup component 12 according to the present disclosure is shown. The acetabular cup component 12 can be used to replace an articulating portion of the anatomy, such as a hip joint. The acetabular cup component 12 can receive and support a bearing or liner that provides an articulating surface. The bearing can be composed of various biocompatible materials including, but not limited to, ceramics, metals and metal alloys, and polymers, such as ultra high molecular weight polyethylene. The bearing can be coupled to the acetabular cup component 12 via known connection methods including, but not limited to, taper lock connection methods and interlocking connection methods.

A suitable interlocking connection can include the Ring-Lac® system commercially available from Biomet, Inc. of Warsaw, Ind. Another suitable connection can include a taper lock connection as discussed in more detail below. In the present example, the acetabular cup component 12 is coupled with a polymer bearing assembly 14 using the RingLac® system. The bearing assembly 14 can include a bearing 16 and a retaining ring 18. The acetabular cup component 12 and the bearing assembly 14 can cooperate with another articulating portion of the anatomy, such as a femoral head prosthesis (FIG. 9) or a native femoral head (not shown).

The acetabular cup component 12 can include an inner shell 20 and a segmented outer shell 22. The inner and outer shells 20, 22 can cooperate and thereby form a bearing engaging surface 24, an annular rim 26, a first interlocking portion 28, an exterior surface 30, and an apical hole 32. The inner shell 20 can include a hemispherical cup 40 and one or more annular rings 42. For example only, the inner shell can include three (3) annular rings 42 as shown. The hemispherical cup 40 can be hemispherical in shape and can include the bearing engaging surface 24 and an outer surface 50. The hemispherical cup 40 can generally have a uniform thickness T1.

The bearing engaging surface 24 can be configured to receive the bearing assembly 14 along a longitudinal axis 52, and to couple the bearing assembly 14 to the acetabular cup component 12. The bearing engaging surface 24 can include a generally smooth, concave surface 54 having a generally uniform radius R1. For example only, the radius R1 can be uniform within about +/−0.5 millimeters (mm), and more specifically uniform within about +/−0.3 mm. In various configurations, the bearing engaging surface 24 can further include portions of the annular rim 26, the apical hole 32, and the first interlocking portion 28. In the present example, the bearing engaging surface 24 includes the annular rim 26, the apical hole 32, and the first interlocking portion 28.

The annular rings 42 can be coupled to the outer surface 50 in any suitable manner, and can be formed integral with the hemispherical cup 40, as shown. The annular rings 42 and the outer surface 50 can define annular recesses 58. The annular rings 42 can protrude from the outer surface 50 in a lateral direction and can extend around, or circumscribe, the hemispherical cup 40 in a continuous manner. The annular rings 42 can laterally extend from the outer surface 50 substantially perpendicular to the longitudinal axis 52. For purposes of the present disclosure, lateral direction will be used generally to refer to a direction transverse to the longitudinal axis 52. Longitudinal direction will be used generally to refer to a direction generally parallel to the longitudinal axis 52. Radial direction will be used generally to refer to a direction along a radius, such as the radius R1.

Figure 9:
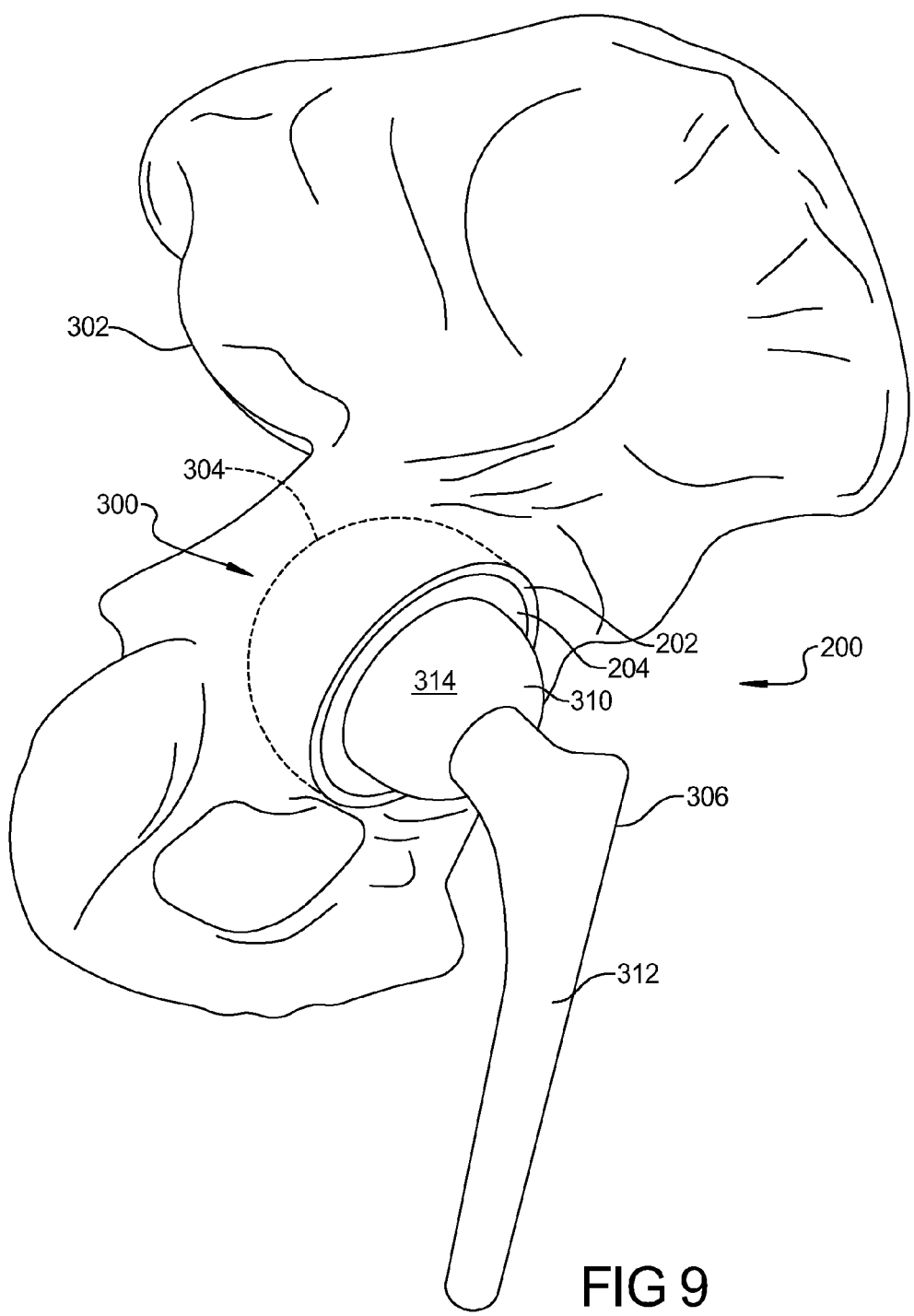
FIG. 9 is an environmental schematic illustration of the hip joint prosthesis of FIG. 7 implanted relative to an anatomy.

The annular rings 42 can include sidewalls 60 and spherical top walls 62. The sidewalls 60 can extend between the outer surface 50 and the exterior surface 30. The sidewalls 60 can be generally parallel as shown or can be angled. The spherical top walls 62 can form first portions of the exterior surface 30 that engage a prepared acetabulum (FIG. 9). The spherical top walls 62 can provide a rough surface that engages the prepared acetabulum when the acetabular cup component 12 is implanted and thereby assists in the fixation of the acetabular cup component 12 within the prepared acetabulum. The annular rings 42 can have thicknesses L1, L2, L3 between the sidewalls 60 and can be spaced apart from the annular rim 26 by distances S1, S2, S3. The thicknesses L1, L2, L3 can be different, or can be equal as shown. The spacing between the annular rings 42 (e.g., S2-S1, S3-S2) can be different, or can be equal, as shown.

The segmented outer shell 22 can be formed on the outer surface 50 in the recesses 58 between the annular rings 42 and can extend around the hemispherical cup 40. Thus, it will be appreciated that the segmented outer shell 22 can include a plurality of annular segments circumscribing the hemispherical cup 40. The segmented outer shell 22 can be formed on the sidewalls 60. The segmented outer shell 22 can extend between the outer surface 50 and the exterior surface 30. The segmented outer shell 22 can form second portions of the exterior surface 30 adjoining the first portions of the exterior surface 30 formed by the annular rings 42, as shown. The segmented outer shell 22 can generally have a uniform thickness T3. The segmented outer shell 22 can be configured to promote bone in-growth into the segmented outer shell 22 and thereby further assist in the fixation of the acetabular cup component 12. For example only, the segmented outer shell 22 can include an interconnected pore structure or porous construct. Regenerex®, a material commercially available from Biomet, Inc. of Warsaw, Ind., is one example of a material having a porous construct. The segmented outer shell 22 can further include a biologically active substance, such as a bone morphogenic protein, a growth factor, a peptide, an antibiotic, and the like.

The inner and outer shells 20, 22 can be composed of various biocompatible materials and can be formed using any suitable processing methods. The inner and outer shells 20, 22 can be coupled using various methods, including but not limited to, adhesive methods, diffusion bonding methods, porous plasma spray coating methods, and sintering methods. According to the present example, the inner shell 20 can be composed of solid Titanium. The segmented outer shell 22 can be composed of Regenerex®. In the present example, the inner shell 20 can be formed using a casting, forging, and/or machining process, while the segmented outer shell 22 can be formed on the inner shell 20 using a sintering process.

In various configurations, the thickness T1 of the hemispherical cup 40 and the number, the thicknesses T2, L1, L2, and L3, and the spacing S1, S2, S3 of the annular rings 42 can be selected to provide the acetabular cup component 12 with a desired overall strength or rigidity, weight, thickness, and finished outside diameter. In a suitable configuration, the thicknesses L1, L2, L3 can be equal and the spacing between the annular rings 42 (e.g., S2-S1, S3-S2) can be equal. When composed of solid Titanium and Regenerex®, the acetabular cup component 12 can have a finished outside diameter of around 58.0 mm. Additionally, a thickness T1 of around 2.5 mm has been found suitable for the hemispherical cup 40, while a thickness T2 of around 1.5 mm has been found suitable for the annular rings 42. Accordingly, the acetabular cup component 12 can have a total thickness of around 4.0 mm or less.

The annular rim 26 can form a laterally extending end face of the acetabular cup component 12 opposite the apex A that engages a complementary rim 70 of the bearing 16. The annular rim 26 can be coupled to the inner shell 20 by any suitable method and can be formed integral with the inner shell 20, such as in the present example.

The first interlocking portion 28 can engage a second interlocking portion 72 of the bearing 16 and thereby couple the bearing 16 to the acetabular cup component 12. The first and second interlocking portions 28, 72 can cooperate to inhibit relative rotational and translational (e.g., longitudinal or lateral) movement between the acetabular cup component 12 and the bearing 16. The first interlocking portion 28 can be coupled to the inner shell 20 by any suitable method and can be formed integral with the inner shell 20, such as in the present example. The first interlocking portion 28 can include a laterally extending first groove 80, a first anti-rotation notch 82, a second anti-rotation notch 84, and one or more anti-rotation tabs 86. For example only, eight (8) anti-rotation tabs 86 are shown.

The first groove 80 can extend between the bearing engaging surface 24 and the exterior surface 30 and can be located between the annular rim 26 and the apex A. The first groove 80 can be sized to slidably receive a portion of the retaining ring 18. The first groove 80 can cooperate with the retaining ring 18 to inhibit relative longitudinal movement between the retaining ring 18 and the acetabular cup component 12 when the bearing 16 is coupled to the acetabular cup component 12.

The first anti-rotation notch 82 can receive a pair of first protrusions 90 formed at an open end of the retaining ring 18 that can be used to grasp and manipulate the retaining ring 18. The second anti-rotation notch 84 can receive and engage a second protrusion 92 of the retaining ring 18 opposite the pair of first protrusions 90. The second anti-rotation notch 84 can cooperate with the second protrusion 92 to inhibit rotation of the retaining ring 18 within the first groove 80 when the bearing 16 is coupled to the acetabular cup component 12.

The anti-rotation tabs 86 can be circumferentially spaced around the annular rim 26 and can engage complementary anti-rotation notches 94 formed in the bearing 16. The anti-rotation tabs 86 can cooperate with the anti-rotation notches 94 to inhibit relative rotational movement between the bearing 16 and the acetabular cup component 12 when coupled.

The second interlocking portion 72 can be coupled to the bearing 16 by any suitable method, and can be formed integral with the bearing 16, as shown. The second interlocking portion 72 can include the anti-rotation notches 94 and a second groove 96. The anti-rotation notches 94 can be formed in and circumferentially spaced around the rim 70. The anti-rotation notches 94 can be sized to provide an interference fit with the anti-rotation tabs 86. The number of anti-rotation notches 94 provided can be equal to or greater than the number of anti-rotation tabs 86 provided. A greater number of anti-rotation notches 94 than anti-rotation tabs 86 can be provided to allow the bearing 16 to be coupled to the acetabular cup component 12 at various rotational positions. The second groove 96 can be formed on an exterior surface of the bearing 16 and can be located adjacent the rim 70. The second groove 96 can receive a portion of the retaining ring 18 and can cooperate with the first groove 80 of the first interlocking portion 28 and thereby longitudinally couple the bearing 16 and the acetabular cup component 12.

The exterior surface 30 can be configured to engage the prepared acetabulum as discussed above and thereby couple the hip joint prosthesis 10 to the prepared acetabulum. According to the present disclosure, the exterior surface 30 can include a convex surface 98 formed by the spherical top walls 62 of the annular rings 42 and adjoining segments of the segmented outer shell 22. The convex surface 98 can have a generally uniform radius R2. For example only, the radius R2 can be uniform within about +/−1.75 mm and, more specifically, uniform within about +/−1.5 mm.

The apical hole 32 can be configured to receive a tool used to implant and/or extract the acetabular cup component 12 within the anatomy. For example, the apical hole 32 can be threaded. The tool can be of any suitable type, such as an impact tool used to press-fit the acetabular cup component 12 in the anatomy. It should be understood, however, that the apical hole 32 is optional, as various other techniques can be employed to couple the acetabular cup component 12 to the anatomy.

As one example, the acetabular cup component 12 can be coupled to the anatomy using a biocompatible adhesive. The apical hole 32 can be formed in the inner shell 20 and/or the segmented outer shell 22 and can extend between the bearing engaging surface 24 and the exterior surface 30, as shown. The apical hole 32 can be formed at any desired location, such as between the annular rim 26 and the apex A. For example only, the apical hole 32 can be located at the apex A, as shown. Although a single apical hole 32 is shown, it should be understood that the acetabular cup component 12 can include a plurality of apertures configured to receive one or more implantation and/or extraction tools. It should be further understood that additional holes can be formed in the acetabular cup component 12 for receiving bone screws used to attach the acetabular cup component 12 to the anatomy.

Figure 4:
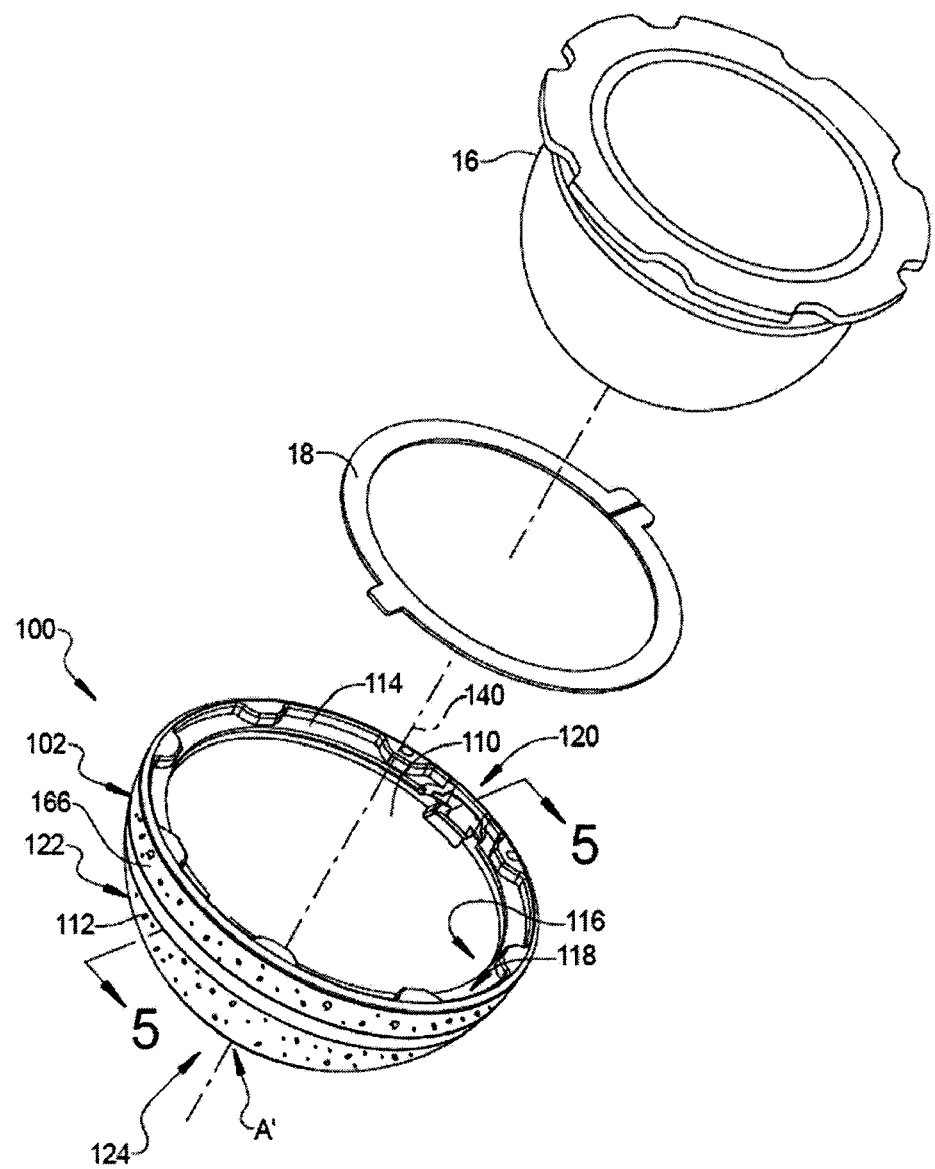
FIG. 4 is a perspective view of another hip joint prosthesis including an acetabular cup component according to the present disclosure.
Figure 5:
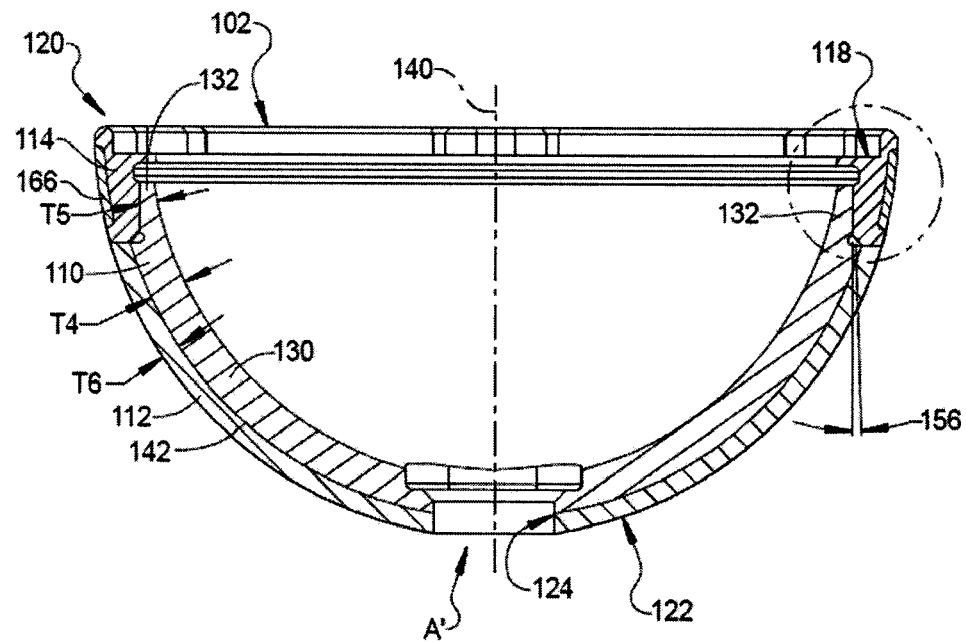
FIG. 5 is a cross-sectional view of the acetabular cup component of FIG. 4 taken along line 5-5.
Figure 6:
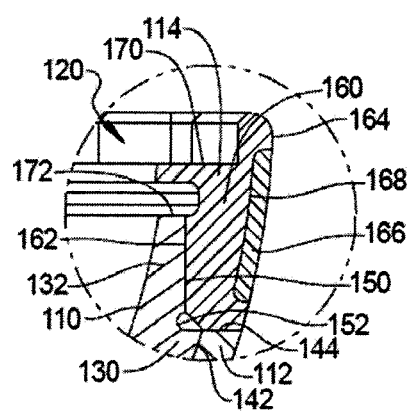
FIG. 6 is an enlarged cross-sectional view of a portion of the acetabular cup component of FIG. 4.

With reference to FIGS. 4-6, another exemplary hip joint prosthesis 100 including an acetabular cup component 102 according to the present disclosure is shown. The acetabular cup component 102 can include an inner shell 110, an outer shell 112, and an annular support ring 114. The inner and outer shells 110, 112 and the annular support ring 114 can cooperate and thereby form an interior surface 116, a rim 118, a first interlocking portion 120, an exterior surface 122, and an aperture 124.

According to the present example, the inner shell 110 can be generally composed of a biocompatible first material having a first stiffness (e.g., modulus of elasticity). The first stiffness can be within around 15 million pounds per square inch (psi). The annular support ring 114 can be generally composed of a biocompatible second material having a second stiffness greater than the first stiffness. Additionally, the annular support ring 114 can couple to an end of the inner shell 110 and can include the rim 118. The annular support ring 114 can be coupled to the inner shell 110 in press-fit arrangement, discussed in more detail below. By forming the annular support ring 114 of a stiffer material and coupling the annular support ring 114 to an end of the inner shell 110, the annular support ring 114 can increase the overall strength or rigidity of the acetabular cup component 102 over other known constructions.

The inner shell 110 can include a hemispherical cup portion 130 and an end portion 132. The hemispherical cup portion 130 and the end portion 132 can be coupled in any suitable manner, and can be integrally formed, as shown. The hemispherical cup portion 130 can be generally hemispherical in shape and can generally have a uniform radial thickness T4. The hemispherical cup portion 130 can have a longitudinal axis 140 extending through an apex A'. The hemispherical cup portion 130 can include a first portion of the interior surface 116, an outer surface 142, and an end face 144. The hemispherical cup portion 130 can further include a portion of the first interlocking portion 120, as discussed in more detail below.

The end face 144 can be a laterally extending surface disposed at an end of the hemispherical cup portion 130. The end face 144 can extend between the end portion 132 and the outer surface 142. In various configurations, the end face 144 can serve as a stop when coupling the annular support ring 114 to the inner shell 110. When coupled, the end face 144 can abut an adjoining lateral surface of the annular support ring 114.

The end portion 132 can longitudinally extend from an end of the hemispherical cup portion 130 opposite the apex A'. The end portion 132 can have a radial thickness T5 less than the radial thickness T4 of the hemispherical cup portion 130. The end portion 132 can include a second portion of the interior surface 116 adjoining the first portion. The end portion 132 can be generally annular in shape and can interlockingly engage the annular support ring 114. The end portion 132 can include a first engagement surface 150 and a relief notch 152 extending between the first engagement surface 150 and the end face 144.

The first engagement surface 150 can frictionally and/or mechanically engage the annular support ring 114. In the present example, the first engagement surface 150 is configured to frictionally engage the annular support ring 114 in the press-fit arrangement discussed in more detail below. The first engagement surface 150 can be a generally smooth, flat surface. The first engagement surface 150 can extend parallel to the longitudinal axis 140. Alternately, the first engagement surface 150 can form an angle with the longitudinal axis 140.

According to the present example, the first engagement surface 150 can form a first taper extending at an angle 156 with respect to the longitudinal axis 140. Thus, it will be appreciated that the radial thickness T5 can decrease with increased distance from the apex A'. In various configurations, the angle 156 can be between around one degree (1°) and twenty-five degrees (25°) and, more particularly, can be between one degree (1°) and seventeen degrees) (17°. In one configuration, the first engagement surface 150 can form a conventional locking taper, such as, for example, a Morse taper. The first engagement surface 150 can be disposed radially outward of the interior surface 116 between the interior surface 116 and the exterior surface 122. In the present example, the first engagement surface 150 is disposed between the interior surface 116 and the outer surface 142.

The outer shell 112 can be formed on the outer surface 142 of the hemispherical cup portion 130. The outer shell 112 can extend around or circumscribe the inner shell 110, as shown. The outer shell 112 can extend between the outer surface 142 and the exterior surface 122 and can include a first portion of the exterior surface 122 as shown. The outer shell 112 can extend between the apex A' and the annular support ring 114 and can engage a lateral surface of the annular support ring 114 adjacent the relief notch 152. The outer shell 112 can be generally hemispherical in shape and can generally have a uniform thickness T6.

The annular support ring 114 can have a continuous, annular or ring-like shape and can be disposed radially outward of the inner shell 110. More specifically, the annular support ring 114 can be disposed radially outward of the end portion 132 of the inner shell 110. The annular support ring 114 can extend around, or circumscribe, the inner shell 110. The annular support ring 114 can extend between the first engagement surface 150 and the exterior surface 122 and can include a second portion of the exterior surface 122 adjoining the first portion.

The annular support ring 114 can include a body 160, a second engagement surface 162, and an outer surface 164. In various configurations, the annular support ring 114 can further include an exterior component 166. The annular support ring 114 can cooperate with the inner shell 110 and thereby include the first interlocking portion 120, as discussed in more detail below.

According to the present disclosure, the body 160 can be a monolithic component composed of a material having a stiffness greater than the stiffness of the material composing the bulk of the inner shell 110. The body 160 can include the second engagement surface 162 and a portion of the outer surface 164. The body 160 can extend between the second engagement surface and the exterior surface 122. The second engagement surface 162 can be complementary to the first engagement surface 150 and can be configured to engage the first engagement surface 150 in a press-fit arrangement. An angular extent of engagement between the first and second engagement surfaces 150, 162 can be three hundred and sixty degrees (360°). The outer surface 164 can be disposed radially outward of the second engagement surface 162 and can be configured to engage the prepared acetabulum. The outer surface 164 can define a recess 168 that receives the exterior component 166.

The exterior component 166 can be formed on the outer surface 164 within the recess 168. Together, the body 160 and the exterior component 166 can form the second portion of the exterior surface 122 adjoining the first portion. The exterior component 166 can be configured to promote bone ingrowth.

Generally, the interior surface 116, the rim 118, the first interlocking portion 120, the exterior surface 122, and the aperture 124 can be substantially similar to the bearing engaging surface 24, the annular rim 26, the first interlocking portion 28, the exterior surface 30, and the apical hole 32, discussed above. Accordingly, the foregoing components of the acetabular cup component 102 will not be discussed in detail, but will be discussed briefly to point out differences. The rim 118 can be formed entirely of the annular support ring 114. Accordingly, the annular support ring 114 can include an end face 170 that engages a portion of a bearing liner (e.g., the bearing 16) when the bearing liner is coupled to the acetabular cup component 102. The annular support ring 114 and the end portion 132 of the inner shell 110 can cooperate to form a groove 172 similar to the first groove 80 of the first interlocking portion 28.

The inner and outer shells 110, 112 and the annular support ring 114 can be composed of various biocompatible materials. According to the present example, the material selected for the annular support ring 114 has a greater stiffness than the material composing the inner shell 110 and the material composing the outer shell 112. As one example, the inner shell 110 can be composed of solid Titanium and the annular support ring 114 can be composed of solid Cobalt or an alloy of Cobalt. The alloys of Cobalt can include cobalt-chromium alloys (CoCr), including cobalt-chromium-molybdenum (CoCrMo) alloys. Generally, Cobalt and alloys of Cobalt will have a stiffness greater than that of solid Titanium. The outer shell 112 can be composed of Regenerex®. When composed of the foregoing materials, a radial thickness T4 of the inner shell 110 of 2.5 mm and a thickness T6 of the outer shell 112 of 1.5 mm have been found suitable.

According to the present example, the inner shell 110 and the annular support ring 114 are coupled in a press-fit arrangement. The annular support ring 114 can be press-fit on the inner shell 110 in any suitable manner. As one example, the annular support ring 114 can be heated to an elevated temperature and thereby expanded. While in the expanded state, the annular support ring 114 can be positioned on the inner shell 110 and allowed to cool, forming the press-fit arrangement. As another example, the inner shell 110 can be cooled by, for example, liquid nitrogen and thereby shrunk. While the inner shell 110 is in the shrunk state, the annular support ring 114 can be positioned on the inner shell 110. Subsequently, the inner shell 110 can be allowed to warm, forming the press-fit arrangement. As yet another example, the annular support ring 114 can be press-fit onto the inner shell by applying a mechanical force along the longitudinal axis 140 and pressing the annular support ring 114 on the inner shell 110.

It should be understood that the outer shell 112 can be formed on the inner shell 110 prior to or after the annular support ring 114 is coupled to the inner shell 110. When the outer shell 112 is formed on the inner shell after the annular support ring 114 is coupled, the outer shell 112 can be formed on both the outer surface 142 of the inner shell 110 and an adjoining portion of the annular support ring 114.

With reference to FIGS. 7-8, another exemplary hip joint prosthesis 200 including an acetabular cup component 202 according to the present disclosure is shown. The acetabular cup component 202 can be configured to receive and support a bearing that provides an articulating surface. The bearing can be coupled to the acetabular cup component 202 via known connection methods including, but not limited to, the RingLac® system described above. In the present example, the acetabular cup component 202 is coupled with a bearing 204 using a taper lock connection. The taper lock connection can provide a frictional and/or mechanical lock coupling the acetabular cup component 202 and the bearing 204.

The acetabular cup component 202 can include an inner shell 206, an intermediate shell 208, and an outer shell 210. The inner, intermediate, and outer shells 206, 208, 210 can cooperate and thereby form an interior surface 212, a rim 214, a first interlocking portion 216, an exterior surface 218, and an apical hole 220. The interior surface 212, the rim 214, the exterior surface 218, and the apical hole 220 can be substantially similar to the bearing engaging surface 24, the annular rim 26, the exterior surface 30, and the apical hole 32, respectively. Therefore, the interior surface 212, the rim 214, the exterior surface 218, and the apical hole 220 will not be described in further detail, except as noted below.

According to the present example, the inner shell 206 can be generally composed of solid Cobalt or an alloy of Cobalt. The intermediate shell 208 can be composed of solid Titanium or an alloy of Titanium. The outer shell 210 can be composed of Regenerex®. When composed in the foregoing manner, the acetabular cup component 202 can have a total thickness of around 4.0 mm or less. Additionally, the intermediate shell 208 can have a first stiffness and the outer shell 210 can have a second stiffness, wherein the first stiffness and the second stiffness are less than a third stiffness of the inner shell 206.

The inner shell 206 can be configured to receive and engage the bearing. The inner shell 206 can be generally hemispherical in shape and can include a first inner surface 222 and a first outer surface 224. The first inner surface 222 can include the interior surface 212 and can be configured to receive the bearing assembly 14 along a longitudinal axis 226. The first outer surface 224 is configured to couple to the intermediate shell 208, and more particularly can be configured to couple to the intermediate shell 208 by a suitable diffusion bonding method. Accordingly, the first outer surface 224 can be a generally smooth surface having a close match to an adjoining surface of the intermediate shell 208. The inner shell 206 can generally have a uniform radial thickness T7. When composed of Cobalt, a radial thickness T7 of around 1.5 mm has been found suitable.

The intermediate shell 208 can be coupled with the inner shell 206 via the first outer surface 224 of the inner shell 206. The intermediate shell 208 can be generally hemispherical in shape and can include a second inner surface 230 and a second outer surface 232. The second inner surface 230 can form the adjoining surface with which the inner shell 206 is bonded. Accordingly, the second inner surface 230 can be complementary with the first outer surface 224 of the inner shell 206, and can be closely matched to the first outer surface 224. The intermediate shell 208 can generally have a uniform radial thickness T8. The radial thickness T8 can be less than the radial thickness T7 of the inner shell 206. When composed of solid Titanium, a radial thickness T8 of around 1.0 mm has been found to be suitable.

The outer shell 210 can be coupled with the intermediate shell 208 via the second outer surface 232. According to the present example, the outer shell 210 can be formed on the second outer surface 232 by sintering. The outer shell 210 can generally have a uniform radial thickness T9. The radial thickness T9 can be greater than the radial thickness T8 of the intermediate shell 208. When composed of Regenerex®, a radial thickness T9 of around 1.5 mm has been found suitable.

The first interlocking portion 216 can cooperate with a second interlocking portion 240 of the bearing 204 and thereby form the taper lock connection coupling the acetabular cup component 202 and the bearing 204. The taper lock connection can form a conventional locking taper, such as, for example, a Morse taper. Accordingly, the first interlocking portion 216 can include a first taper 242 that frictionally engages a second taper 244 of the bearing 204. The first taper 242 can be formed on the interior surface 212. Generally, the first taper 242 can be formed adjacent the rim 214. The first taper 242 can form an angle 246 with the longitudinal axis 226. In various configurations, the angle 246 can be between around one degree (1°) and twenty-five degrees (25°) and, more particularly, can be between one degree (1°) and seventeen degrees)(17°.

The second taper 244 can be formed on an exterior surface 250 of the bearing 204 and can frictionally engage the first taper 242 of the acetabular cup component 202 when the bearing 204 is coupled with the acetabular cup component 202. The second taper 244 can complement the first taper 242. Accordingly, in various configurations, the second taper 244 can form an angle between around one degree (1°) and twenty-five degrees (25°) and, more particularly, between around one degree (1°) and seventeen degrees (17°) with the longitudinal axis 226 when coupled with the acetabular cup component 202.

With additional reference to FIG. 9, an exemplary use of the acetabular cup components 12, 102, 202 in an exemplary total hip replacement procedure will now be described. For simplicity, the use will be described with reference to the acetabular cup component 202. However, it will be appreciated that a substantially similar procedure can be used for the acetabular cup components 12, 102. Generally, an acetabulum 300 of a pelvis 302 can be prepared to include a hemispherical socket 304 by known methods. For example, the socket 304 can be prepared by reaming the acetabulum 300 with a reamer (not shown). An exemplary method of preparing an acetabulum by reaming is described in commonly assigned U.S. Patent Application Publication No. 2007/0203583, the disclosure of which is incorporated by reference herein.

With the anatomy prepared, the acetabular cup component 202 can be implanted in the socket 304 and coupled to the pelvis 302. The acetabular cup component 202 can be coupled to the hip bone by any suitable method, including but not limited to, press-fit methods, adhesive methods, etc. In one example, the acetabular cup component 202 can be coupled to the pelvis 302 by press-fitting the acetabular cup component 202 in the socket 304. A tool used for press-fitting and/or impacting the acetabular cup component 202 can be coupled to the acetabular cup component 202 via the apical hole 220. An exemplary press-fitting method is also disclosed in U.S. patent application Ser. No. 11/365,895, previously incorporated by reference herein. Although not specifically shown, the acetabular cup components 12, 102, 202 can include additional bone engagement features that protrude from the exterior surface. In configurations including bone engagement features, the press-fitting of the acetabular cup component 202 can drive the engagement features into the adjoining anatomy of the pelvis 302 to further couple the acetabular cup component 202 to the anatomy.

With the acetabular cup component 202 coupled to the pelvis 302, the bearing 204 can be inserted within and coupled to the acetabular cup component 202. The bearing 204 can be inserted along the longitudinal axis 226 and coupled to the interior surface 212 via the taper lock connection formed by the first and second interlocking portions 216, 240. In the present example, the bearing 204 can be coupled by engaging the first and second tapers 242, 244.

With the bearing 204 and acetabular cup component 202 coupled to the pelvis 302, an adjoining articulating surface provided for a femur (not shown) associated with the pelvis 302 can be brought into engagement with the bearing 204. The articulating surface can be provided by a femoral head prosthesis 306 as shown or, alternatively, by a native femoral head (not shown). It will be appreciated that the present disclosure is not limited to femoral head prostheses of a particular type.

As one example, the femoral head prosthesis 306 can include a head component 310 and a stem component 312. The head component 310 can be coupled to the stem component 312. The head component 310 can generally be spherical in shape and can include an articulating surface 314. The stem component 312 can be coupled to the femur. With the femoral head prosthesis 306 coupled to the femur, the head component 310 can be guided into engagement with the bearing 204 and thereby engage the acetabular cup component 202.

From the foregoing it will be appreciated that the reduced overall thicknesses (e.g., T1+T2 of the acetabular cup component 12) of the acetabular cup components 12, 102, 202 can enable the acetabular cup components 12, 102, 202 to have interior surfaces 24, 116, 212 of increased radii (e.g., radius R1 of the acetabular cup component 12). In turn, the acetabular cup components 12, 102, 202 can enable the use of associated bearings (e.g., the bearing 16 of the bearing assembly 14, bearing 204) and adjoining articulating surfaces (e.g., the articulating surface 314 of the head component 310) of increased radii or diameters.

The ability to use larger femoral head components can increase the range of motion of a femoral head prosthesis relative to the acetabular cup components 12, 102, 202. The ability to use larger femoral head components can also reduce the dislocation of the acetabular cup components 12, 102, 202 within the socket 304.

It will further be appreciated that the reduced overall thicknesses of the acetabular cup components 12, 102, 202 can enable the acetabular cup components 12, 102, 202 to have exterior surfaces 30, 122, 218 or reduced radii (e.g., radius R2 of the exterior surface 30) for a given radius or diameter of a femoral head component. In turn, the reduced radii of the exterior surfaces 30, 122, 218 can reduce the amount of bone material that is removed from the acetabulum 300 to prepare the socket 304 during implantation procedures. The ability to reduce the amount of bone material removed can enable less invasive procedures involving the pelvis 302.

The foregoing description of the examples has been provided for purposes of illustration and description. It is not intended to be exhaustive or to limit the present disclosure. Individual elements or features of a particular example are generally not limited to that particular example, but, where applicable, are interchangeable and can be used in a selected example, even if not specifically shown or described. The same may also be varied in many ways. Such variations are not to be regarded as a departure from the spirit and scope of the present teachings, and all such modifications are intended to be included within the scope of the present disclosure.

What is claimed is:

1. An acetabular cup component for replacing an articulating portion of an anatomy, comprising:
    a bearing liner;
    a first shell including:
        a hemispherical cup portion forming an interior surface and an outer surface opposite the interior surface, the interior surface configured to receive the bearing liner along a longitudinal axis of the hemispherical cup portion extending through an apex of the hemispherical cup portion; and
        an end portion longitudinally extending from an end of the hemispherical cup portion opposite the apex, the end portion including an engagement surface disposed on an outer circumference of the end portion;
    a second shell having means for permanently connecting the first shell at the outer surface of the hemispherical cup portion and circumscribing the hemispherical cup portion, the second shell including a first portion of an exterior surface configured for contacting an acetabulum; and
    a support ring coupled to the end portion via the engagement surface, the support ring including a second portion of the exterior surface configured for contacting the acetabulum and a rim for engaging the bearing liner, wherein the support ring defines an annular recess in the exterior surface, and wherein the acetabular cup component further comprises an exterior component disposed in the annular recess and configured to promote bone in-growth.

2. The acetabular cup component of claim 1, wherein the support ring engages the engagement surface in a press-fit.

3. The acetabular cup component of claim 1, wherein the engagement surface forms a first taper with respect to the longitudinal axis and the support ring includes a complementary second taper that engages the first taper in a press-fit.

4. The acetabular cup component of claim 1, wherein the support ring abuts a laterally extending end face of the hemispherical cup portion adjacent the engagement surface.

5. The acetabular cup component of claim 1, wherein the end portion defines a relief notch extending between the engagement surface and the hemispherical cup portion.

6. The acetabular cup component of claim 1, wherein the support ring is composed of Cobalt.

7. The acetabular cup component of claim 1, wherein the support ring has means for permanently connecting the engagement surface.

8. The acetabular cup component of claim 1, wherein the support ring includes a ring surface configured to engage the engagement surface in a press-fit.

9. An acetabular cup component for replacing an articulating portion of an anatomy, comprising:
   a bearing liner;
   a first shell including:
      a hemispherical cup portion forming an interior surface and an outer surface opposite the interior surface, the interior surface configured to receive the bearing liner along a longitudinal axis of the hemispherical cup portion extending through an apex of the hemispherical cup portion; and
      an end portion longitudinally extending from an end of the hemispherical cup portion opposite the apex, the end portion including an engagement surface disposed on an outer circumference of the end portion;
   a second shell fixedly connected to the first shell at the outer surface of the hemispherical cup portion and circumscribing the hemispherical cup portion, the second shell including a first portion of an exterior surface configured for contacting an acetabulum; and
   a support ring coupled to the end portion via the engagement surface, the support ring including a second portion of the exterior surface configured for contacting the acetabulum and a rim for engaging the bearing liner, wherein the support ring defines an annular recess in the exterior surface, and wherein the acetabular cup component further comprises an exterior component disposed in the annular recess and configured to promote bone in-growth.

10. The acetabular cup component of claim 9, wherein the first shell and the second shell are fixedly connected by one of adhesively adhering, diffusion bonding, porous plasma spray coating, or sintering.

11. The acetabular cup component of claim 9, wherein the engagement surface forms a first taper with respect to the longitudinal axis and the support ring includes a complementary second taper that engages the first taper in a press-fit.

12. The acetabular cup component of claim 9, wherein the support ring abuts a laterally extending end face of the hemispherical cup portion adjacent the engagement surface.

13. The acetabular cup component of claim 9, wherein the end portion defines a relief notch extending between the engagement surface and the hemispherical cup portion.

* * * * *